United States Patent [19]

Leopoldi et al.

[11] 4,452,243

[45] Jun. 5, 1984

[54] SANITARY BLOOD LANCET DEVICE

[75] Inventors: Norbert Leopoldi, Chicago; William P. Heinrich, McHenry, both of Ill.

[73] Assignee: Cloverline, Inc., Chicago, Ill.

[21] Appl. No.: 354,374

[22] Filed: Mar. 3, 1982

Related U.S. Application Data

[63] Continuation-in-part of Ser. No. 284,603, Jul. 20, 1981, abandoned.

[51] Int. Cl.³ .............................................. A61B 17/34
[52] U.S. Cl. .................................. 128/314; 128/329 R
[58] Field of Search ................... 128/314, 315, 329 R, 128/330, 770, 763, 346; 24/252 A

[56] References Cited

U.S. PATENT DOCUMENTS

| | | | |
|---|---|---|---|
| 236,084 | 12/1880 | Reinhold et al. | 128/314 |
| 262,833 | 8/1882 | Rosenberg | 128/329 R |
| 2,467,487 | 4/1949 | Leon | 24/252 A |
| 3,358,689 | 12/1967 | Higgins | 128/329 |
| 3,659,608 | 5/1972 | Perry | 128/314 |
| 3,874,042 | 4/1975 | Eddleman et al. | 128/346 X |
| 3,913,584 | 10/1975 | Walchle et al. | 128/329 R X |
| 4,230,118 | 10/1980 | Holman et al. | 128/314 |
| 4,324,248 | 4/1982 | Perlin | 128/346 X |

FOREIGN PATENT DOCUMENTS

| | | | |
|---|---|---|---|
| 626062 | 8/1927 | France | 128/329 R |

Primary Examiner—Michael H. Thaler
Attorney, Agent, or Firm—McWilliams, Mann, Zummer and Sweeney

[57] ABSTRACT

The invention comprises a blood lancet device for puncturing the fleshy part on the inner side of a finger tip, or an ear lobe, in order to draw blood for a hemoglobin test, or other type of blood test and which is completely sanitary to avoid any possibility of contamination of the blood drawn for testing. The device includes a finger grip element to be held by a user, with a surface adapted to be engaged with the fleshy finger tip pad, or ear lobe, and a hinged striker element pivotally mounted on the device and spring actuated to drive a sharp puncturing element secured on the striker, into such pad, with a thumb piece on the striker for drawing it back to a cocked position and having a twist-off or tear away protective element for maintaining the sanitary condition of the puncturing element until it is to be used. The striker element is flexible and the finger grip element is provided with an upstanding projection on the top surface, which the striker contacts and about which the striker flexes when it is spring actuated downwardly about its pivot, whereby the puncturing element is thrust downwardly below the bottom surface of the finger grip element to puncture the flesh and then be retracted upwardly when it rebounds to dispose the puncture element substantially above such bottom surface in a withdrawn position.

3 Claims, 9 Drawing Figures

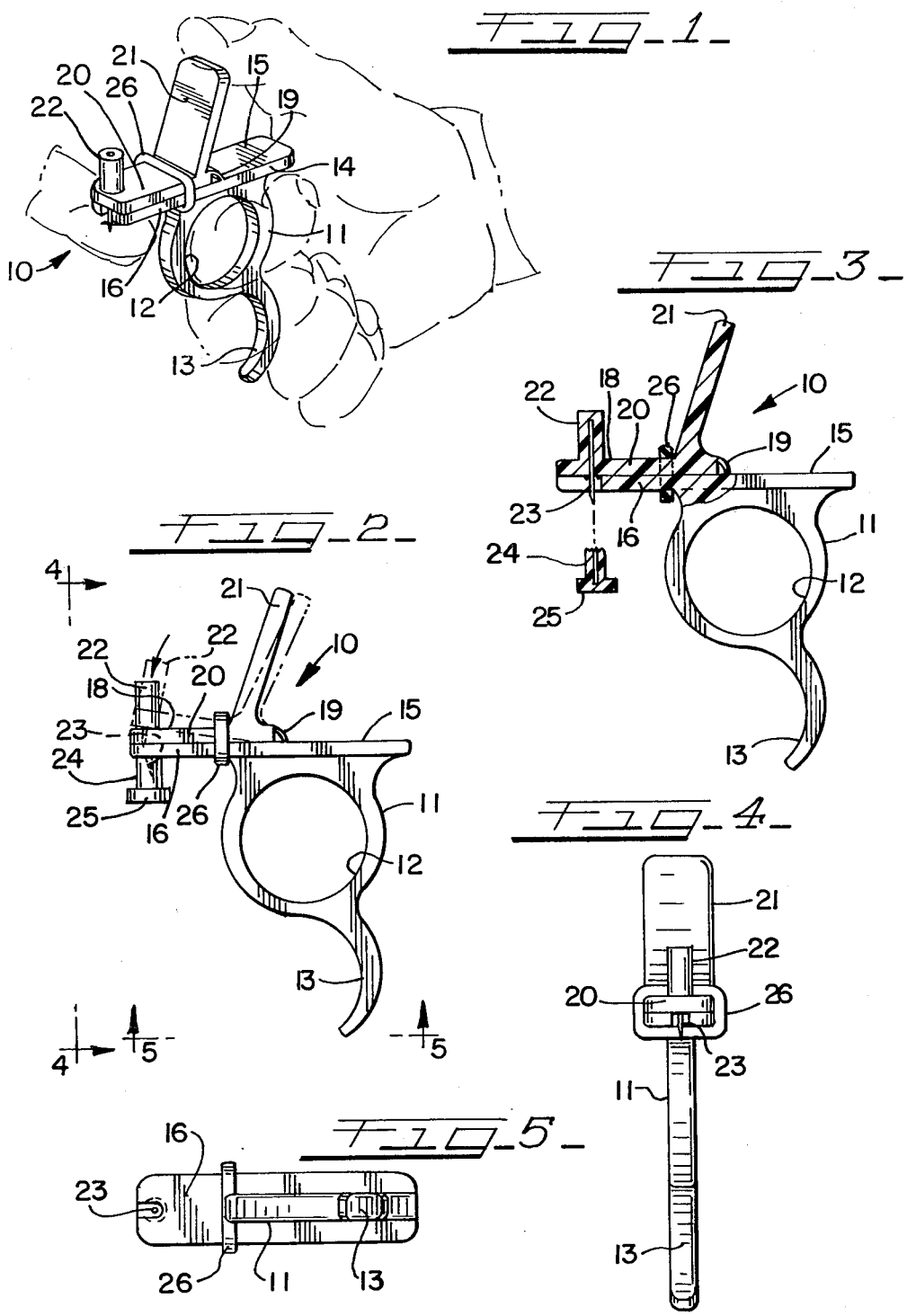

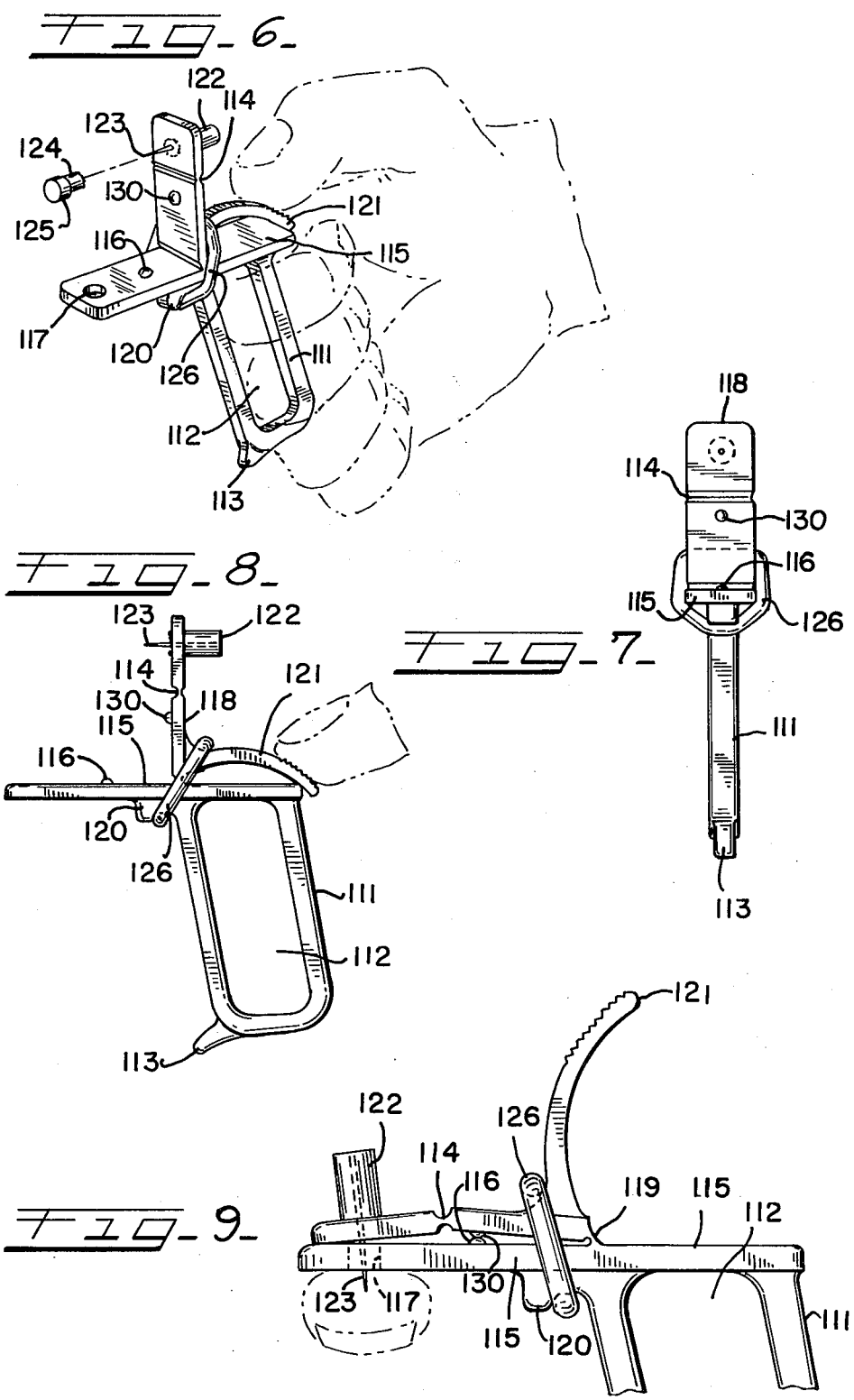

SANITARY BLOOD LANCET DEVICE

This application is a continuation-in-part of our application Ser. No. 284,603, filed July 20, 1981, now abandoned.

BACKGROUND OF THE INVENTION

Heretofore, blood has been drawn from a patient for testing by puncturing the finger tip pad at the fleshy inner side of the finger by cutting the pad with a sharp knife, or a needle and this puncture was made by a quick jab of the puncturing element into the finger pad to cause bleeding. However, this operation was not always accurately performed and resulted in unnecessarily hazardous penetration of the flesh and painful reaction by the patient.

The finger to be punctured was tightly held by the nurse, or technician performing the operation and sometimes the users of this method would miss the finger pad of the patient and jab their own finger and create a possibility of serious contamination by mixing two blood types, or by contaminating the puncturing instrument itself. Some prior devices have been spring driven in an axial direction to puncture the finger tip pad by a knife, or pin, that first had to be retracted to cock the puncturing device and when released was forcefully driven into the pad, sometimes unnecessarily deep and at times striking the bone with attendant pain to the patient.

Some doctors, or nurses, have at times drawn blood for testing by using a knife, or scalpel, with which they made a cut into the finger pad, but this too was painful to the patient and sometimes left a wound that entailed a prolonged period of healing. All such prior methods of drawing blood for tests were somewhat haphazard and entailed risks and pain to the patient and the devices, where utilized for repeated use, necessarily had to be sterilized before each use.

SUMMARY OF THE INVENTION

This invention provides a hinged striker element of flexible construction for driving a sharp puncturing device into the fleshy finger tip pad, or an ear lobe and which is integrally associated with a mounting element that includes a generally flat surface member on which the striker element is pivotally secured for hinged movement with an upward projection on the flat surface about which the striker flexes when it is swung from a cocked position to an operative position where its travel is limited by engagement with the flat surface element.

The flat surface member is provided with a finger hold portion at the opposite side from the hinged striker mounting and preferably this includes a hole for insertion of one finger of a user and a trigger-like part for engagement by a second finger. The striker element has an angularly disposed thumb piece by means of which the striker may be cocked against force exerted by an elastic element that forcefully moves the striker to its operative position when the thumb piece is released.

The striker element also has an enclosure, or mounting, for a needle preferably, or a knife, or other sharp instrument, to puncture the finger pad under impact driven by the elastic element. The puncturing element is mounted adjacent the free end of the striker and the actual puncturing part extends through an opening in the flat surface element to engage the finger pad.

The opening through the flat surface element comprises a slot in the end area of the element and when the sharp puncturing element passes through this slot under impetus of the elastic when the thumb piece is released, its depth of penetration into the finger pad is limited by the thickness of the flat surface member which is placed on the finger pad, with the striker cocked, to position the striker for proper entry of the puncturing part into the finger pad. A fulcrum-like upward projection on the flat surface causes the puncturing element to flex thereabout when this element is impelled by the elastic and thereby project through the slot and penetrate the finger pad after which it is retracted by the elastic to dispose the sharp element at least within the thickness of the flat surface member, or thereabove. The sharp puncturing part is maintained in a completely sanitary condition prior to use by being fully enclosed within the closure mounting until actual use is to be made of the device to draw blood.

The striker element is provided with a hinge point intermediate its length to facilitate flexing thereof when it contacts the upward projection atop the flat surface element, whereby the puncturing element more readily passes through the surface element and into the flesh to be punctured and by the same token is sprung back to its normally retracted position.

This puncturing part is exposed just before use by removing a tear-off part, or a twist-off piece, forming the actual enclosure about the puncture part and this is done before the striker is cocked and then the striker is cocked and the flat surface member laid on the finger pad and the thumb piece released to let the puncture part strike the fulcrum-like projection and flex about its hinge point to project the puncturing element through the slot and into the flesh of the finger pad and thus cause the finger to bleed.

The entire puncturing device is made from a suitable plastic material for ease of manufacture and especially economy, so that the device can be used for but one blood drawing operation and then discarded. The elastic element comprises a relatively heavy band of rubber, or other elastic material, for this same purpose, whereby the entire assembly is very cheap to produce and can economically be thrown away after one use.

The elastic element encircles the striker element and the flat surface member at the side of the hinge toward the free end, so that when the striker is cocked the elastic is stretched and when the thumb piece is released the stressed elastic band exerts a force on the striker to impact the striker about the fulcrum projection to cause the sharp element to be propelled through the slot and puncture the finger pad which is disposed against the flat bottom surface on the member when that type of blood test is to be made.

DESCRIPTION OF THE DRAWINGS

The principal objectives of the invention are attained by the arrangement and structure of the device illustrated in the accompanying drawings wherein FIG. 1 is a general perspective view of the finger puncturing device showing the sanitary enclosure of the puncture element removed and its mounting in a hinged striker element integral with a finger hold part and illustrating the device as held by a user with a finger under the extension piece for puncture;

FIG. 2 is a side elevational view of the finger puncturing lancet showing the striker in the closed position with the sanitary closure still in place;

FIG. 3 also is a side elevational view with portions in section and showing the sanitary closure broken away to expose the lancet device;

FIG. 4 is an end elevational view of the device with the enclosure removed and the lancet device exposed ready for use;

FIG. 5 is a bottom plan view of the device with the closure removed;

FIG. 6 is a general perspective view of the preferred form of the invention, illustrating the lancet device as held by a user, showing the device in its cocked condition with its sanitary cover for the puncturing element removed and the hinged striker element provided with an intermediate hinge area for flexibility;

FIG. 7 is a front elevational view of the lancet also in the cocked position;

FIG. 8 shows a side elevational view with the striker cocked; and

FIG. 9 is a side view, to larger scale, with the striker actuated to the puncturing position, where the puncture device projects through the finger contacting element into the finger.

DESCRIPTION OF FIRST EMBODIMENT

In the drawings the numeral 10 is a general reference character directed to the finger puncturing assembly as a whole and the reference 11 identifies the finger hold piece having a finger hold 12 and a trigger shaped finger piece 13. This finger hold piece is integral with a generally flat surface member 14 that has a flat upper surface 15 and which extends beyond the finger hold portion as at 16. The free end of the extension 16 has an open slot 17 that extends entirely through the thickness of the extension and is open through the end of the extension for a purpose hereinafter to appear.

A striker member 18 is pivotally mounted on the flat surface member 14 approximately midway of its length and pivots about an integral hinge 19 that comprises a relatively thin section of the same plastic material with the finger hold 11 and the member 14 so that the striker is freely movable from operative to cocked position.

The striker includes a strike portion 20 disposed substantially parallel with the force of the surface member 14 and a thumb piece 21 disposed at an angle extending upwardly from adjacent the hinge end of the striker, so that in its generally upright position it forms an open angle with the flat upper surface of member 14 and whereby the thumb piece can be pivoted backwardly about the hinge 19 until the free end thereof comes into contact with the surface of the flat member 14.

At its free end the striker has an integral enclosure piece 22, which in the form shown has a needle 23, or other flesh puncturing instrument embedded, or secured therein and actually is molded into the enclosure when it is made. At the bottom end of the enclosure the instrument 23 is fully enclosed for sanitary purposes by means of a hollow tubular section 24 that covers the instrument 23 on all sides and extends through the slot 17 at the free end of the flat member extension 16.

The tubular section 24 is a tear-away item molded integrally with the enclosure 22 which of course is integral with the puncturing device as a whole. The tear-away portion of the tubular section is of thinner section than the rest of the tubular structure and may measure in the range of about 0.005" to about 0.008" so that by twisting the section this thin section will tear away and the tubular member can be removed to expose the instrument 23. The tubular section 24 can readily be twisted by means of an integral headed portion 25 on the lower end of the section and thus torn away from the lower side of the striker member 18.

An important feature of this finger puncturing device resides in the type of force applying means to snap the striker 18 from its cocked position, with the thumb piece against the upper surface of the flat member 14, to the finger puncturing position with the instrument 23 extending through the slot 17 and limited as to its penetration of the finger pad, or ear lobe, by the thickness of the extension 16 which rests on the surface to be punctured. The force applying means is very simple in operation and very economical in the manufacture and assembly of the puncturing device as a complete unit to arrive at a device of this type which may easily be considered a throw-away item after one use.

The force applying means is comprised of a relatively heavy band 26 of rubber, or other elastic material, that encircles the striker 20 and the extension 16 on the member 14 so that when the striker is cocked, the band 26 is stretched and thus placed under tension to develop a force that snaps the striker into engagement with the upper surface of flat 14 with the instrument 23 projecting through the slot 17 into the finger pad, when the thumb piece 21 is released and thus enable the finger puncturing device to complete its function.

In practice a nurse, or doctor, or other technician, using this invention to puncture a patient's finger tip, or ear lobe, to draw blood for testing, will grasp the finger grip elements 12 and 13 in one hand, twist off the protective cover 24 with the other hand to expose the lancet 23, cock the striker 20 by actuating the thumb piece 21 with the thumb of the hand holding the device and while holding the finger, or ear lobe to be punctured, with the other hand, lay the extension 16 on the surface where it is desired to draw blood and release the thumb piece, whereupon the lancet 23 will be snapped to its operative position projecting through the slot 17 and puncturing the flesh, with the slotted extension piece 16 limiting the degree of penetration by the striker contacting the top surface 15 of the extension and immediately after the puncturing operation the lancet 23 will be retracted by the action of the elastic 26.

DESCRIPTION OF PREFERRED EMBODIMENT

As shown in FIGS. 6-9, the preferred form of the invention utilizes an elongated finger hold piece 111 which has a similarly shaped opening 112 for receiving one or more fingers of the user to provide a stable means of holding the lancet and for convenient cocking of the hingedly mounted striker member 118. A generally horizontal shelf, or flat surface 115 is shown as integral with the finger piece 111 and which extends substantially beyond the finger hold piece, as best shown in FIG. 8. Adjacent the free end of the shelf 115 a hole 117 extends entirely throuqh the shelf for the passage of a puncturing instrument 123 during the operation of letting blood from a patient's finger, as indicated in FIG. 9.

The striker element 118 is pivotally mounted on the shelf 115, as at 119 and this hinge element is integral with the shelf and with the striker. The striker 118 pivots on the shelf 115 at a point approximately midway of the length of the shelf so that the striker engages the free end area of the shelf in the finger puncturing position shown in FIG. 9 and a thumb piece 121 on the striker engages the opposite end area of the shelf when the striker is cocked, as shown in FIG. 8. An anti-fingerslipping projection 113 is provided at the front side of the finger hold 111 to prevent the fingers from slipping off when they are engaged around the front side of the finger hold instead of through the central opening.

An important feature of the striker element 118 comprises an intermediate hinge point 114 that is integral with the striker and represents a thin section therein that enables the striker to flex more readily when it is released from its cocked position whereby the puncture element 123 is easily driven through the opening 117 by the force applied by the spring device 126 which actually comprises a heavy rubber band that encircles the striker element 118 and the shelf 115 so that the band is placed under tension when the striker is cocked and then expends this built-up force when the thumb piece 121 is released and thereby rapidly advance the striker to cause the puncturing element 123 to pass through the opening 117 and puncture the flesh under the shelf 115, as in FIG. 9.

The sharp puncture element 123 is integrated with the striker 118 by molding it integrally with an enclosure 122 formed as a part of the striker 118 and disposed at the upper side thereof. The sharp end of the puncture element 123 below the shelf 115 is also enclosed for maintaining the sanitary condition of this part and this enclosure comprises a tubular section 124 that comprises a removable, or tear-away portion, for easy disposal when the lancet is prepared for use. The tear-away portion 124 may be of thin section material so that by twisting the section it may readily be torn off to expose the sharp puncture device 123. In order to make such removal of the protective cover 124 more readily attainable it is provided with an integral head portion 125 of larger diameter that may be grasped and twisted to tear the cover away from the lower side of the shelf 115 and thus expose the sharp puncture element for use.

The force generating tension device 126 encircles the striker element in the bight area where the thumb piece 121 and the shelf 118 are joined and at the under side of the shelf the tension device encircles the shelf between the finger-hold element 111 and a depending projection 120 on the under side of the shelf, thus accurately positioning the member 126 at the location where it is most effective to exert the maximum effort in actuating the striker. To facilitate the flexing of the striker at the hinge point 114 projections 116 and 130 are provided on the upper surface of the shelf 115 and the under side of the striker 118 respectively, so located that when the thumb piece 121 is released to actuate the striker under the impetus of the spring 126, the two projections will engage to stop the downward arcing of the striker portion between the hinges 114 and 119 and cause the free end portion of the striker beyond the hinge 114 to swing forceably about this hinge point and drive the puncture element 123 through the shelf opening 117 and thereby quickly complete the puncturing operation.

CONCLUSION

From the foregoing it will be seen that a blood lancet device has been provided which is made entirely of plastic materials for economy of manufacture and having an elastic force generating means to actuate a hinged striker and containing a sharp flesh penetrating instrument to create a wound from which blood can be drawn for test purposes, whether it be a hemoglobin test, blood type, or other test. The striker importantly is pivotally mounted and self-hinged on a finger hold element that includes a fulcrum-like upward projection about which a built-in hinge point of the striker flexes and also affords a convenient means for a user to hold the device from which to operate the striker.

What is claimed is:

1. A flesh puncturing device for creating a wound from which blood can be drawn for testing, said device having a pivoted striker member including a puncturing instrument, and a finger hold member supporting the striker member, said striker and finger hold members including an integral hinge portion connecting the two parts for hinging of the striker on the finger hold member, said finger hold member having a generally flat member and an extension generally parallelling said striker member, a tension member operatively engaging said striker member and said extension and placed under increased tension when the striker moves away from the extension, said striker having an acutely angled thumb piece disposed closely adjacent to said hinge portion for moving the striker away from the extension to cock the striker, said finger hold member includes a finger hold located beneath said flat portion, said finger hole having an integral lower finger portion by means of which the device is held by a user, said integral hinge portion being disposed substantially midway of said generally flat member and said thumb piece is retracted toward said flat member to cock the striker member, said pivoted striker member being flexible and said extension member has a top surface including an upward projection about which the striker member flexes when impelled by said tension member and is retracted by the tension member after puncturing a finger pad.

2. A flesh puncturing device as set forth in claim 1 wherein said pivoted striker member has a relatively thin section intermediate its length to provide a built-in hinge point to facilitate flexing of the striker about said projection.

3. A flesh puncturing device as set forth in claim 2 wherein said strike member has a downward projection cooperating with said upward projection on said top surface.

* * * * *